United States Patent
Brunner et al.

(10) Patent No.: US 10,302,497 B2
(45) Date of Patent: May 28, 2019

(54) METHOD AND DEVICE FOR THE THERMAL ANALYSIS OF A SAMPLE AND/OR FOR THE CALIBRATION OF A TEMPERATURE MEASURING DEVICE

(71) Applicant: Netzsch-Gerätebau GmbH, Selb (DE)

(72) Inventors: Martin Brunner, Konradsreuth (DE); Alexander Schindler, Leupoldsgruen (DE); André Lindemann, Merseburg (DE)

(73) Assignee: Netzsch-Gerätebau GmbH, Selb (DE)

( * ) Notice: Subject to any disclaimer, the term of this patent is extended or adjusted under 35 U.S.C. 154(b) by 170 days.

(21) Appl. No.: 15/379,012

(22) Filed: Dec. 14, 2016

(65) Prior Publication Data

US 2017/0176257 A1 Jun. 22, 2017

(30) Foreign Application Priority Data

Dec. 17, 2015 (DE) .................. 10 2015 122 037

(51) Int. Cl.

| | | |
|---|---|---|
| *G01K 15/00* | (2006.01) | |
| *G01N 25/18* | (2006.01) | |
| *G01K 1/16* | (2006.01) | |
| *G01J 5/02* | (2006.01) | |
| *G01J 5/10* | (2006.01) | |
| *G01N 25/20* | (2006.01) | |
| *G01J 5/00* | (2006.01) | |

(52) U.S. Cl.
CPC ............ *G01J 5/025* (2013.01); *G01J 5/0255* (2013.01); *G01J 5/10* (2013.01); *G01N 25/18* (2013.01); *G01N 25/20* (2013.01); *G01J 2005/0048* (2013.01); *G01J 2005/0085* (2013.01)

(58) Field of Classification Search
USPC ...................................... 374/1, 120, 44, 141
See application file for complete search history.

(56) References Cited

U.S. PATENT DOCUMENTS

| | | | |
|---|---|---|---|
| 6,551,835 B1* | 4/2003 | Schawe ............. | G01N 25/4833 374/10 |
| 2006/0039443 A1 | 2/2006 | Watanabe et al. | |
| 2008/0208546 A1* | 8/2008 | Hutter ................ | G01N 25/4833 703/2 |
| 2013/0336355 A1* | 12/2013 | Neumann ............. | G01N 25/20 374/10 |

FOREIGN PATENT DOCUMENTS

| | | |
|---|---|---|
| DE | 4131040 A1 | 3/1993 |
| DE | 4301987 A1 | 7/1994 |
| DE | 102012106955 A1 | 2/2014 |

(Continued)

OTHER PUBLICATIONS

Tm M Manuelian et al: "Thermal Diffusivity, Specific Heat, and Thermal Conductivity Measurement Using Netzsch LFA 447 Nanoflash", Published: May 16, 2008 8 Pages.

(Continued)

*Primary Examiner* — Mirellys Jagan
(74) *Attorney, Agent, or Firm* — Whitmyer IP Group LLC (57) ABSTRACT

A method and a device for the thermal analysis of a sample, as well as a method and a device for the calibration of a temperature measuring device used in a device for the thermal analysis.

14 Claims, 3 Drawing Sheets

(56) References Cited

FOREIGN PATENT DOCUMENTS

JP        H09159631 A    6/1997

OTHER PUBLICATIONS

European Search Report Application No. 16002330.5 Completed Date May 24, 2017; dated Jun. 2, 2017 11 Pages.
David Gilbers et al: "Charakterisierung und Validierung des Laser-Flash-Verfahrens zur Bestimmung der Temperaturleitfahigkeit im Temperaturbereich bis 2000° C." Published: Mar. 18, 2013 Translation of Slides on pp. 3 and p. 5. 1 Page.
Translation Excerpt of European Search Report Related to Reference D4 (David Gilbers et al) Application No. 16002330.5 Completed Date May 24, 2017; dated Jun. 2, 2017 2 pages.

\* cited by examiner

Fig. 5

METHOD AND DEVICE FOR THE THERMAL ANALYSIS OF A SAMPLE AND/OR FOR THE CALIBRATION OF A TEMPERATURE MEASURING DEVICE

TECHNICAL FIELD

The invention at hand relates to a method and a device for the thermal analysis of a sample, as well as a method and a device for the calibration of a temperature measuring device used in a device for the thermal analysis.

BACKGROUND

In the thermal analysis, material characteristics are investigated by means of a sample from the respective material as a function of the temperature. A correct thermometry, that is, a correct measuring of the temperature of the sample, thus plays an important role.

Temperature sensors, e.g. in the form of thermal elements or electrical resistance thermometers, which can be arranged in thermal contact to the sample, e.g., so as to measure the temperature of the sample, are known from the prior art for this purpose.

This measuring, however, is more or less error-prone depending on the temperature program, that is, the change of the sample temperature provided during the thermal analysis, because the temperature sensor does not measure the temperature in the interior of the sample, but on an edge of the sample.

This measuring error is even more significant for temperature sensors (which are used in many cases), which cannot be arranged in direct contact to the sample, but which are instead arranged adjacent to the sample, thus spatially separated therefrom, inside a temperable sample chamber.

This problem can be reduced significantly by means of a suitable "calibration" of the used temperature sensor or of the temperature measuring device formed therewith, respectively. For such a calibration, provision can be made, e.g., to measure the temperature of one or a plurality of samples, which melt in response to temperatures, which are known in each case, in the course of a temperature program in the respective device for the thermal analysis, so as to then calibrate the temperature measuring device or the temperature sensor, respectively, by comparing the measured melting temperatures to the melting temperatures, which are known (e.g. from the literature).

It is a disadvantage, however, that such a calibration of the temperature measuring device is relatively extensive. In spite of the calibration, the measured temperature is also not necessarily representative of the average sample temperature in the sample interior, because more or less large temperature gradients can be present in the sample, depending on the temperature program. A further disadvantage can be that the calibration is no longer correct and a systematic error occurs in the temperature measuring, when changing the position of the temperature sensor even only slightly.

In the case of the known thermometry in the context of a thermal analysis, whether with or without calibration of the above-described type, it is further disadvantageous that many temperature sensors, such as, e.g., thermal elements and resistance thermometers, are oftentimes not stable over a long period of time, but change their characteristics over time due to aging and/or contamination.

SUMMARY

It is an object of the invention at hand to specify a novel way, by means of which the accuracy and reliability of a measuring of the temperature of a sample can be improved in the context of a thermal analysis conducted on this sample.

According to a first aspect of the invention, the latter starts at a method for the thermal analysis of a sample, which comprises:

tempering the sample according to a temperature program, in the course of which a temperature of the sample is changed, measuring the temperature of the sample in the course of the temperature program, measuring at least one physical characteristic of the sample, which differs from the temperature of the sample, in the course of the temperature program.

To solve the above-mentioned object, this method according to the invention is characterized in that the measuring of the temperature of the sample comprises:

irradiating a first surface area of the sample with an electromagnetic excitation beam, detecting an intensity of a thermal radiation emanating from a second surface area of the sample as a result of the irradiation, determining a temperature conductivity of the sample by evaluating the detected intensity of the thermal radiation, determining the temperature of the sample by means of the determined temperature conductivity by using data, which specify the temperature-dependent course of the temperature conductivity of the sample.

In combination, the steps of an irradiation of a first surface area of the sample with an electromagnetic excitation beam, detecting an intensity of a thermal radiation emanating from a second surface area of the sample as a result of the irradiation, as well as a determining of the temperature conductivity of the sample by evaluating the detected intensity of the thermal radiation as provided in the context of the invention, will also be identified hereinafter in short as "flash method".

The basic idea of the invention is thus to initially determine a temperature conductivity of the sample by means of the method, which is also often identified as "flash method" in the prior art, so as to then draw a conclusion to the temperature of a sample by means of the determined temperature conductivity by using data (known from the literature, e.g., or from other measurements, e.g.), which specify the temperature-dependent course of this temperature conductivity.

The tempering of the sample can be carried out, e.g., by means of a sample chamber, which can be heated in a controlled manner and/or which can be cooled in a controlled manner, and in which the sample is accommodated during the measuring, e.g., in an accommodation of a sample holder.

The control of an electric heating and/or cooling device, e.g., provided for this purpose can be carried out, e.g. in a program-controlled manner by means of a control device, such as a microcontroller or the like, wherein the temperature program provided hereby, that is, a certain time-dependent course of the temperature, can either be accomplished by means of a simple control of the heating or cooling output, respectively, or by means of a control of the heating or cooling output, respectively, which is regulated on the basis of the measuring of the temperature of the sample.

In one embodiment, a change of the temperature of the sample by at least 100 k, in particular by at least 200 K, is provided in the course of the temperature program.

The temperature program can provide for an underlying course of the temperature, that is, a linear temperature change with regard to the time-dependency, or a different time-dependent course of the temperature. In the alternative or in addition to a substantially constant underlying temperature change rate, a temperature modulation (e.g. sinusoidal) can also be provided in the course of the temperature program.

In addition to the measuring of the temperature of the sample, at least one further physical characteristic of the sample, which differs from the temperature of the sample, is also measured in the course of the temperature program. In addition to the already mentioned temperature conductivity (e.g., measured by means of the mentioned flash method), a force exerted on the sample and/or a dimension (e.g. length or thickness of a sample), shall be mentioned herein only in an exemplary manner, which are both relevant, e.g. in response to a so-called thermo-mechanical analysis or dilatometry, respectively, and the (optical) reflectivity of the sample surface.

The term "temperature conductivity" used herein is to identify a physical characteristic, which quantifies a temporal and/or spatial change of the spatial distribution of the temperature and/or of the heat by means of heat conduction as a result of a temperature drop. This includes in particular the temperature conductivity $\alpha$ in a narrower sense, as it is defined as $\alpha = \lambda / \rho \times c$, wherein $\lambda$ identifies the heat conductivity of the sample,
$\rho$ identifies the density of the sample, and
$c$ identifies the specific heat capacity of the sample.

The heat conductivity $\lambda$ included in the above definition is hereby the proportionality factor of the heat flow density as a function of the temperature gradient:

$dQ/dt = \lambda \times A \times (\Delta T/L)$, wherein $dQ/dt$ identifies the heat flow,
A identifies the cross sectional surface, through which the heat flow flows,
L identifies the thickness of the layer, through which the heat flow flows, and
$\Delta T$ identifies the temperature difference between the edge surfaces of the layer with the thickness L.

According to the above statements, it shall not be ruled out that a variable, which is mathematically associated with the above-defined "temperature conductivity $\alpha$", such as, e.g., the above-defined "heat conductivity $\lambda$", is used as "temperature conductivity" in terms of the invention.

It is significant for the invention in this respect that the temperature conductivity determined by evaluating the detected intensity of the thermal radiation, has the same definition or physical meaning, respectively, as the temperature conductivity, the temperature-dependence of which is specified by means of the data, which are used according to the invention in response to the temperature determination.

The irradiation preferably takes place by means of an excitation pulse or, in the course of the temperature program, by means of a sequence of excitation pulses, for example with a pulse duration of less than 100 ms, in particular of less than 50 ms.

The irradiation can be carried out by means of a flash lamp, e.g. (e.g. halogen flash lamp) or by means of a laser (which is preferably operated in a pulsed manner).

The electromagnetic excitation beam can have, e.g., dominating spectral portions in the visible and/or infrared area.

The irradiation can take place by means of an irradiation current density, e.g., which is uniform across the first surface area of the sample. This first surface area can be circular, e.g., and can be provided on a flat side of a platelet-shaped sample, e.g., or can be formed by the (entire) such flat side. The second surface area of the sample is preferably not identical with the first surface area and is preferably located on a side of the sample located opposite the first surface area.

If the event that a platelet-shaped sample is used, the first and second surface areas are preferably arranged on the flat sides of the sample located opposite one another or are formed by these flat sides, respectively.

The detection of the intensity of the thermal radiation emanating from the second surface area of the sample can be carried out, e.g., by means of an imaging detector (less preferable) or (preferably) by means of an infrared (IR) detector, which detects the thermal radiation cumulatively.

An optical system, in particular an optical imaging system, in particular comprising at least one refractive element and/or at least one reflective element, can be provided between the sample and a detector, which is used to detect the thermal radiation intensity, and/or between the sample and an irradiating source (e.g., flash lamp or laser), which is used to irradiate the sample. A beam guidance of the excitation beam and/or of the thermal radiation to be detected, which increases the accuracy of the flash method, can be realized in an advantageous manner with this.

In one embodiment, the method is carried out on a platelet-shaped sample (e.g. comprising a round shape), wherein the platelet-shaped sample has a uniform thickness, viewed across the surface thereof (e.g. in the range of between 0.1 and 6 mm).

The material of the sample can be a metallic material or a semiconductive material. The invention is particularly suitable for samples comprising a temperature conductivity $\alpha$ in the range of above $1 \times 10^{-6}$ m$^2$/s, for example in the range of between $1 \times 10^{-6}$ m$^2$s and approximately $5 \times 10^{-4}$ m$^2$/s).

The determination of the temperature conductivity of the sample by evaluating the detected intensity of the thermal radiation can advantageously take place by using all of the methods, which are known for this from the prior art relating to flash methods. On principle, a physical-mathematical model is used, which describes the sample, including at least the temperature conductivity of the sample as a model parameter, by means of which a course of the thermal radiation intensity measured in a time-dependent manner is used to determine the model parameter "temperature conductivity" (and/or at least one model parameter, which allows for the calculation of this temperature conductivity) by means of a mathematical equalizing calculation ("fit"). A corresponding calculation of the temperature conductivity of the sample is preferably carried out by means of a program-controlled data processing device, which can in particular be a control device, e.g. which is provided for controlling (e.g. all) controllable components of a respective device for the thermal analysis.

The determination of the temperature of the sample by means of the determined temperature conductivity by using data, which specify the temperature-dependent course of the temperature conductivity of the sample, can advantageously also be carried out by means of a program-controlled data processing device, e.g. the mentioned control device. Preferably, the device used for the determination has a storage unit, in which the required data for determining the sample temperature are stored (e.g. in addition to a program code required for the operational control (e.g. control of the temperature program and of the irradiation source used in the flash method)). These data can be stored, e.g., in the form of a (digital) "lookup table", so that the corresponding temperature (e.g. determined in advance from the literature) can be read from this table for a certain temperature conductivity.

In the case, which is rather rarer in practice, that (due to a corresponding sample material) a determined temperature conductivity cannot be assigned clearly to a corresponding temperature, and in the event that a plurality of different temperatures comprising the same assigned temperature conductivity are in fact reached in the course of the temperature program, it is sufficient in the context of the determination of the sample temperature to carry out a corresponding "rough determination" of the temperature in a suitable manner, so as to reach a clear allocation of the correct temperature on this basis. Aside from a conventional temperature measuring device provided for this purpose, the rough determination of the temperature can for the most part already be accomplished from the characteristics or the control, respectively, of the concrete temperature program as well.

Based on the already mentioned known method for the thermal analysis of a sample, comprising:

tempering the sample according to a temperature program, in the course of which a temperature of the sample is changed, measuring the temperature of the sample in the course of the temperature program, measuring at least one physical characteristic of the sample, which differs from the temperature of the sample, in the course of the temperature program.

It is proposed according to a further aspect of the invention that the measuring of the temperature of the sample comprises:

arranging a further sample adjacent to the sample, so as to subject the sample and the further sample to the tempering together, irradiating a first surface area of the further sample with an electromagnetic excitation beam, detecting an intensity of a thermal radiation emanating from a second surface area of the further sample as a result of the irradiation, determining a temperature conductivity of the further sample by evaluating the detected intensity of the thermal radiation, determining the temperature of the sample by means of the determined temperature conductivity of the further sample by using data, which specify the temperature-dependent course of the temperature conductivity of the further sample.

The advantage of this method is that, in contrast to the method, which has already been described above, no data are required, which specify the temperature-dependent course of the temperature conductivity of the sample.

In the case of this invention alternative, the basic idea is to subject (at least) one "further sample" to a common tempering, together with the "actual" sample, that is, the sample, which is to be analyzed thermally, in the context of the same thermal analysis, so as to then use the further sample quasi as a vehicle for the realization of a sample temperature measuring of the already described type. It is sufficient for this that the data, which specify the temperature-dependent course of the temperature conductivity of the further sample, are known or are provided, respectively (it is assumed in this alternative that the sample and the further sample always have the same temperature).

Aside from the existence and the common tempering of the "further sample" as well as the use of the data provided for this further sample relating to the temperature-dependent temperature conductivity, all of the special embodiments and designs described for the method described above according to the first aspect of the invention, can analogously also be provided as embodiments or designs, respectively, of the method according to the second aspect of the invention. This also relates in particular to the already described device components and technical features of such device components, which can be provided for carrying out the individual method steps.

The only thing, which needs to be taken into account hereby, is that the flash method provided in the method according to the second aspect of the invention is carried out on the further sample (and only optionally on the sample) in any event. A sample holder provided for storing the further sample can be arranged in such a manner in this respect with regard to a used excitation beam source and with respect to a used thermal radiation detection device that the irradiation and the detection occur (only) on the further sample.

In a further development of the method, it is provided that a change (preferably controlled automatically) between a plurality of the samples, which are subjected to the common tempering, is used in the course of the temperature program by using a sample changing device in such a manner that a selected sample can in each case be subjected to the flash method by using a (single) irradiation source and a (single) thermal radiation detection device. A simple implementation of this embodiment is the use of a so-called sample changer, for example of a sample holder, which can be rotated in the manner of a revolver, comprising a plurality of accommodations for simultaneously accommodating a plurality of samples, one sample of which can in each case be brought into the beam path of the irradiating device and of the detection device, depending on the rotational position of the sample changer.

If applicable, (at least) one "sample" can be subjected to the thermal analysis, including the flash method, as part of this analysis by means of such a sample change or the use of such a sample changer, respectively, in an advantageous manner, e.g. within the same measuring process or temperature program, respectively, and (at least) one "further sample" can be subjected to this flash method by means of the means for carrying out the flash method, which are present in any event in this case, for the purpose of measuring the temperature of the (at least) one sample.

The control of a sample changer can be carried out in a program-controlled manner, e.g. by means of the mentioned control device.

In the event that a plurality of "further samples" (of the same or different material) are used to determine the temperature of the "sample" by using the flash method by using the respective data (which differ from one another, if applicable), a redundancy can be created in an advantageous manner when determining the sample temperature, and the temperature, which is determined in the end, can be provided on this basis, e.g. as an average value of the temperatures, which result for the individual "further samples" by means of the results of the determination.

According to a third aspect of the invention, a method for the calibration of a (e.g. "conventional") temperature measuring device, which is used in a device for the thermal analysis of a sample, is used to measure a temperature of the sample, comprising:

arranging a sample in the device for the thermal analysis, tempering the sample according to a temperature program, in the course of which a temperature of the sample is changed, measuring the temperature of the sample in the course of the temperature program by means of the temperature measuring device, (additional) measuring of the temperature of the sample in the course of the temperature program by means of the following steps:

irradiating a first surface area of the sample with an electromagnetic excitation beam, detecting an intensity of a thermal radiation emanating from a second surface area of the sample as a result of the irradiation, determining a temperature conductivity of the sample by evaluating the detected intensity of the thermal radiation, determining the temperature of the sample by means of the determined temperature conductivity by using data, which specify the temperature-dependent course of the temperature conductivity of the sample, calibrating the temperature measuring device by means of a comparison of results of the two measurements of the temperature of the sample.

Aside from the existence and use of a temperature measuring device used to measure a temperature of the sample (and the latter method of a calibration of this temperature measuring device), this method according to the third aspect of the invention obviously comprises method steps, in which embodiments or designs, respectively, as they have already been described above for the method according to the first and the second aspect of the invention, can be used analogously as special embodiments or designs, respectively, in an advantageous manner.

The arrangement of the sample can thus be carried out, e.g. by using a sample holder, which comprises a single accommodation for accommodating a sample and which is accommodated in a temperable sample chamber of the device. If a calibration of the temperature measuring device is to be carried out by means of this sample, this requires the data, which specify the temperature-dependent course of the temperature conductivity of this sample. If, however, the temperature measuring device has already been calibrated in this manner, a sample of a (known or unknown) material can also be subjected to a thermal analysis by means of the same device (without hereby requiring such data).

In the alternative, a sample change can take place, e.g. by means of a sample changer, which can be operated in a controlled manner, which at least has two (or more) accommodations. This is already advantageous, because a plurality of samples can be thermally analyzed by means of this in a (single) measuring process (temperature program), whether in the case of an already calibrated temperature measuring device by using the temperature measuring device for measuring the temperature of the sample in the course of the temperature program, or in the event that a calibration of the temperature measuring device has not yet taken place, or took place too long ago, respectively, with a simultaneous calibration of the temperature measuring device (in that at least one of the samples is used as sample for the additional temperature measuring by means of the flash method and is used for the subsequent calibration of the temperature measuring device after the temperature program has concluded).

According to a fourth aspect of the invention, a device comprising means for carrying out a method for the thermal analysis of a sample and/or for the calibration of a temperature measuring device included in such a device, is proposed.

All of the embodiments and designs, which have already been explained above, can be considered for the concrete design of the means (device components), According to an exemplary embodiment of a device for the thermal analysis of a sample, this device comprises:

a sample chamber comprising a sample holder accommodated therein for arranging (at least) one sample in the sample chamber, a tempering device comprising a heating device and/or a cooling device for tempering the sample according to a temperature program, in the course of which a temperature of the sample is changed, (optionally) a measuring device for measuring at least one physical characteristic of the sample, which differs from the temperature of the sample, in the course of the temperature program, an irradiating source for irradiating a first surface area of the sample with an electromagnetic excitation beam, a detection device for detecting an intensity of a thermal radiation emanating from a second surface area of the sample as a result of the irradiation, an evaluation device for determining a temperature conductivity of the sample by evaluating the detected intensity of the thermal radiation, in particular a program-controlled evaluation device (e.g. embodied as part of a control device, which controls all of the controllable device components), preferably comprising a storage unit for storing data, which specify the temperature-dependent course of the temperature conductivity of the (at least one) sample, wherein the evaluation device is further embodied to determine the temperature of the sample by means of the determined temperature conductivity by using the mentioned data.

In particular the method according to the first aspect of the invention can be carried out by means of this embodiment.

To make it possible to carry out the method according to the second aspect (as an alternative or in addition to the possibility of carrying out the method according to the first aspect), a further sample holder for accommodating (at least) one "further sample" and/or a multiple sample holder (in particular, e.g. displaceable or rotatable sample changer) comprising a plurality of accommodations is required. It must furthermore be provided that the (at least) one "further sample" can be subjected to the flash method for determining the sample temperature by means of the irradiation source, the detection device and the evaluation device.

To make it possible to carry out the method according to the third aspect of the invention (as an alternative or in addition to the methods according to the first and/or second aspect), the device requires a temperature measuring device, which is to be calibrated (e.g. comprising at least one thermal element and/or at least one resistance thermometer or the like). On principle, one sample holder is sufficient to accommodate a (single) sample, wherein a multiple sample holder or a sample changer, which can be operated in a controlled manner, is also advantageous in the case of this embodiment.

According to a fifth aspect of the invention, a computer program product comprising a program code is proposed, which carries out a method of the type described here on a data processing device, in particular, e.g. the mentioned control device of the device.

BRIEF DESCRIPTION OF THE DRAWINGS

The invention will be described in more detail below by means of exemplary embodiments with reference to the enclosed drawings.

DETAILED DESCRIPTION

Figure 1:
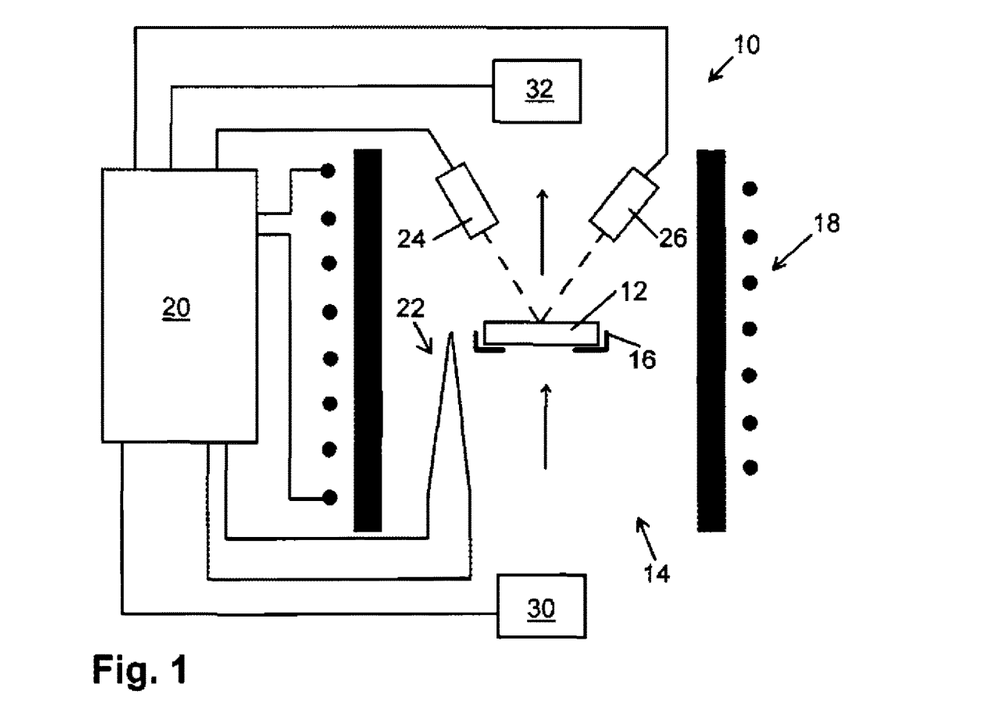
FIG. 1 shows a device for the thermal analysis of a sample according to an exemplary embodiment.

FIG. 1 shows, schematically, a device 10 for the thermal analysis of a sample 12, comprising a sample chamber 14 comprising a sample holder 16 accommodated therein for accommodating the sample 12. To temper the sample 12 according to a predetermined temperature program, in the course of which a temperature T of the sample 12 is changed, the device 10 in the illustrated example comprises an electric heating device 18, which is controlled by a central control device 20 of the device 10 according to the predetermined temperature program.

The control device 20 is embodied as a program-controlled control device (micro-controller) and is equipped with a (non-illustrated) human-machine interface, via which a user can provide details of the temperature program, e.g. a start and end temperature, as well as details for the control of components, which will be described below, to the device 10.

To measure the temperature T of the sample 12 in the course of the temperature program, the device 10 comprises a thermal element 22, which is accommodated in the sample chamber 14 and by means of which the control device 20 carries out a measuring of the sample temperature T and stores time-resolved data relating to the temperature in the sample chamber 14 and thus the sample temperature T, in a digital storage device of the control device 20.

The thermal analysis carried out on the sample 12 serves to determine at least one physical characteristic (which differs from the sample temperature T) of the sample 12 as a function of the sample temperature T.

With regard to the measuring of such a physical characteristic, an optical transmitter 24 and an optical detector 26, which are also connected to the control device 20 as illustrated, are illustrated only in an exemplary manner, so as to measure a corresponding measuring of the physical characteristic (e.g. optical reflectivity, change in length of the sample, etc.), and to store time-resolved data relating to this physical characteristic in the storage device of the control device 20.

The measuring device formed in this example by the components 24 and 26 is to only be understood in an exemplary manner. In this respect, all of the measuring devices, which are known from the prior art of thermal analyses, can be used for embodying the measuring device in the context of the invention (e.g. also for measuring a force acting on the sample or for measuring the sample mass, etc.).

During or after completing the temperature program, data relating to the temperature dependency or a temperature-dependent course of the respective physical characteristic, respectively, can be generated, stored in the control device 20, and can be provided to the user for a further evaluation.

In the case of the device 10, the accuracy of the measuring of the sample temperature T, which is realized by means of the thermal element 22, is problematic on principle. It turned out to be advantageous in practice to carry out a calibration of this temperature measuring device from time to time (and/or after changing the temperature program), so as to increase the accuracy of the temperature measuring, which is carried out therewith.

To carry out a calibration of the temperature measuring, the device 10 comprises means for carrying out a "flash method" on a sample, which is held by the sample holder 16. These means comprise an irradiation source 30 (here, e.g. a laser, which is controlled by the control device 20 in a pulsed manner), by means of which a first side (bottom side in FIG. 1) of the sample is heated by means of electromagnetic excitation pulses, and a detection device 32 for detecting an intensity of a second side (upper side in FIG. 1) of the sample opposite the first side of the sample as a result of the thermal radiation emanating from the irradiation.

The detection device 32 (here an IR detector, e.g.) is connected to the control device 20 as illustrated, so as to provide a detector signal, which is representative of the thermal radiation intensity, to the control device 20. The flash method realized by means of the components 30 and 32 works as follows: a platelet-shaped sample, of which the temperature-dependent course of the temperature conductivity α is known, is initially placed into the sample holder 16. The control device 20 in connection with the heating device 18 then generate or start, respectively, different temperatures in the sample chamber 14 according to a predetermined temperature program, and measuring them by means of the thermal element 22. For example, this can in particular be a completion of that temperature program, by means of which a sample 12 is to be analyzed thermally after the calibration has ended. The sample, which serves as "temperature measuring reference" is heated from the bottom side by means of short irradiation pulses from the irradiation source 30 in the course of the temperature program. Each such irradiation pulse has the result that a temperature rise results on the upper side of the sample after a certain temporal offset. The temperature conductivity α of the sample follows directly from the transient course of the temperature rise, which is measured by means of the detection device 22, by using a suitable mathematical model, which is stored in the control device 22 or which can be predetermined on the user side, respectively, and with the knowledge of a thickness of the sample.

The detected thermal radiation intensity is thus evaluated in the control device 20 so as to determine the temperature conductivity α of the sample (for every temperature rise resulting from an irradiation pulse), and to store it in allocation to the temperature T, which is measured simultaneously by means of the thermal element 22. Data relating to the sample temperature T are furthermore generated in the control device 20 by using the data, which specify the temperature-dependent course of the temperature conductivity of the sample, so that temperature measuring results, from the temperature measuring device, which is realized by means of the thermal element 22 on the one hand and from the temperature measurement by means of the flash method on the other hand are at hand in the course of the tempering for a plurality of sample temperatures T. The calibration of the temperature measuring device, which is realized by means of the thermal element 22, then takes places by means of the measuring results, which were determined by means of the flash method, so that more accurate measuring results are provided for the sample temperature T in subsequent temperature measurements by means of the thermal element 22. The characteristic of the conversion of a thermoelectric voltage, which is provided by the thermal element 22, into the corresponding temperature is adapted concretely in response to this calibration, in the illustrated example. The idea, on which the calibration is based, is thus to draw a conclusion to the temperature in the interior of the sample from the measuring of the temperature conductivity α of a sample with known temperature-dependent course of the temperature conductivity α.

A more accurate sample temperature T with a slight systematic deviation, better robustness and long-term stability follows in an advantageous manner by means of the flash method.

In contrast to the example illustrated in FIG. 1, the measuring device for the temperature-dependent measuring of the mentioned physical characteristic of the sample could also be formed by the means (which are present in any event) for carrying out the flash method, here thus the irradiation source 30 and the detection device 32. In this case, the device 10 can serve, e.g., for the temperature-dependent measuring of temperature conductivity α on different samples 12. The control device 22 in connection with the components 30 and 32 can then also be embodied to carry out the described method for the calibration of the temperature measuring device, which is embodied with the thermal element 22.

In contrast to the example illustrated in FIG. 1, a "conventional" temperature measuring device (here: thermal element 22) can even be foregone completely in the case of the device 10. Such an example of a device will be described below with reference to FIG. 5.

Several aspects relating to the accuracy of the "temperature conductivity thermometer", which is used in the context of the invention (formed from the components 30, 32 and 20) will be explained below.

The accuracy is examined in the form of an uncertainty "u". An uncertainty u(T) of the sample temperature T, which is determined by means of the flash method, can be expressed as follows:

$$u(T)=(d\alpha/dT)^{-1} \times u(\alpha) \quad \text{(equation 1)}$$

whereby u(T) identifies the uncertainty of the temperature T, and dα/dT identifies the increase of the temperature-dependent temperature conductivity α.

It can be seen from equation 1 that the uncertainty u(T), which is to be expected, is smaller, the more α depends on T. For many materials, this is increasingly so even for lower temperatures T, which is illustrated in FIG. 2 by means of some example materials.

Figure 2:
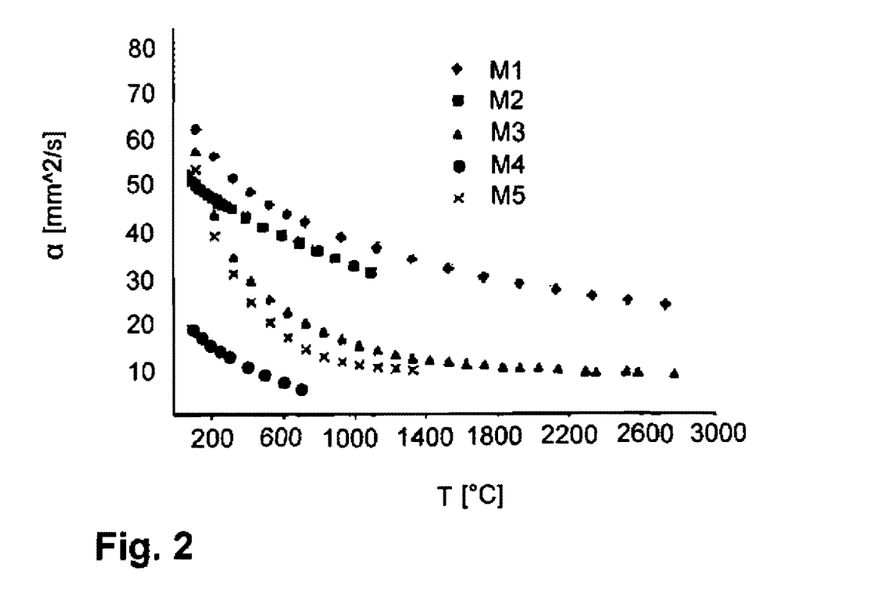
FIG. 2 shows an application of the temperature conductivity α as a function of the temperature, for different materials (literature values)

FIG. 2 shows an application of the temperature conductivity α as a function of the temperature T for a number of different materials M1 (tungsten), M2 (molybdenum, type "SRM781", M3 (graphite), M4 (iron) and M5 (silicon).

All of the materials M1 to M5, which are mentioned in an exemplary manner here, are suitable for use in the context of the invention at hand, in particular at temperatures T of less than 1000 K.

Figure 3:
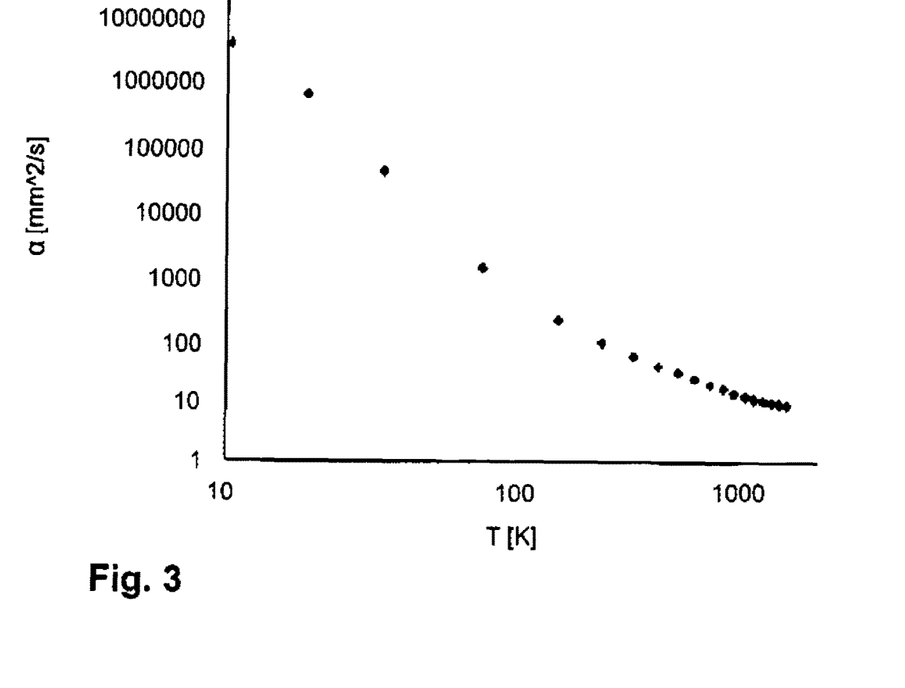
FIG. 3 shows a double-logarithmic application of the temperature conductivity α of silicon as a function of the temperature (literature values)

The temperature conductivity α of silicon (material M5) as a function of the temperature T for a larger temperature range is once again illustrated in FIG. 3 in a double-logarithmic application.

It can be seen from this that the use of silicon for measuring temperature by means of the flash method is advantageous all the way to very low temperatures T. The temperature conductivity α increases by approximately five magnitudes as the temperature drops between room temperature (approx. 300 K) and 10 K.

In one embodiment, provision is thus made to provide silicon as material for the sample, which is used for this temperature measuring.

Returning once again to the above-specified equation 1, it can also be seen from this that the uncertainty u(T) is smaller, the smaller the uncertainty u(α) of the temperature conductivity α. When determining the sample temperature T from the comparison of a temperature conductivity $\alpha_{mess}$ measured in the flash method, with corresponding literature values $\alpha_{lit}$, the following can be assumed for u(α):

$$u(\alpha)=\sqrt{u^2(\alpha)_{lit}+u^2(\alpha)_{mess}} \quad \text{(equation 2)}$$

whereby $u(\alpha)_{lit}$ identifies the uncertainty of the temperature conductivity $\alpha_{lit}$ (literature values), and $u(\alpha)_{mess}$ identifies the uncertainty of the temperature conductivity $\alpha_{mess}$ (measuring values)

The uncertainty $u(\alpha)_{lit}$ of the literature values is typically in the range of between 5% and 15%, whereas the uncertainty $u(\alpha)_{mess}$ of the measured temperature conductivity $\alpha_{mess}$ is typically in the range of approx. 3%.

In this case, the total resulting uncertainty u(α) of the "temperature conductivity thermometer" is determined largely by the uncertainty $u(\alpha)_{lit}$ of the literature values (or of the values represented by the "data" in the case of the invention) of the temperature conductivity α.

In a further development of the invention, provision is made for the temperature conductivity thermometer to be calibrated via a calibrated different thermometer.

In a further embodiment, a plurality of temperature conductivity thermometers of the same type are calibrated via a calibrated further thermometer, so as to obtain an averaged "master curve" <α(T)> of the temperature conductivity thermometer type. Systematic uncertainties, e.g. due to the uncertainty of the sample thickness, but also uncertainties due to endless reproducibility of the temperature conductivity measuring can be reduced. With such an embodiment, the uncertainty u(α) is reduced to:

$$u(\alpha)=\sqrt{i^2(\alpha)_{kal}+u^2(\alpha)_{repr}} \quad \text{(equation 3)}$$

wherein the uncertainties of the calibration of the temperature conductivity thermometer are combined in $u(\alpha)_{kal}$, and $u(\alpha)_{repr}$ is the uncertainty due to endless reproducibility of the temperature conductivity measurement when reading the temperature conductivity thermometer. In a further design, the latter can be reduced in that an average is formed when reading via a plurality of temperature conductivity thermometers (which is very practicable, e.g. when using a controllable sample changer, in particular by means of a sample changer, which can be controlled automatically by means of a control device of the device) and/or when an average is formed via a plurality of measurements on a temperature conductivity thermometer.

As a whole, a value of approximately 1% of the measuring value α can be strived for u(α). If u(α)=1%×α is assumed, the uncertainty u(T) of the temperature conductivity thermometer illustrated in FIG. 4 results in the case of silicon as "thermometer material" (material of the sample, which is subjected to the flash method).

Figure 4:
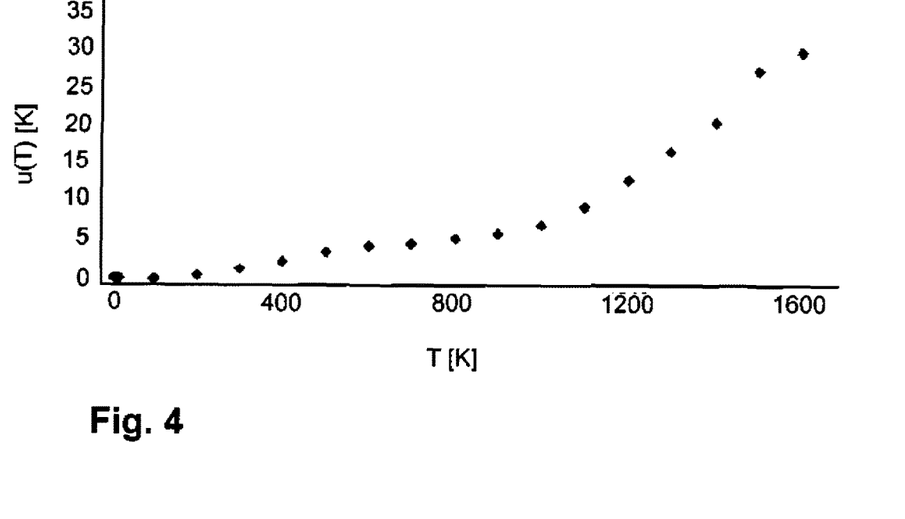
FIG. 4 shows an application of an uncertainty of a temperature measurement as a function of the temperature when using a flash method on a sample of silicon.

It can be seen from this that an uncertainty u(T) of less than 1 K can be reached in the temperature range below room temperature (approx. 300 K).

Figure 5:
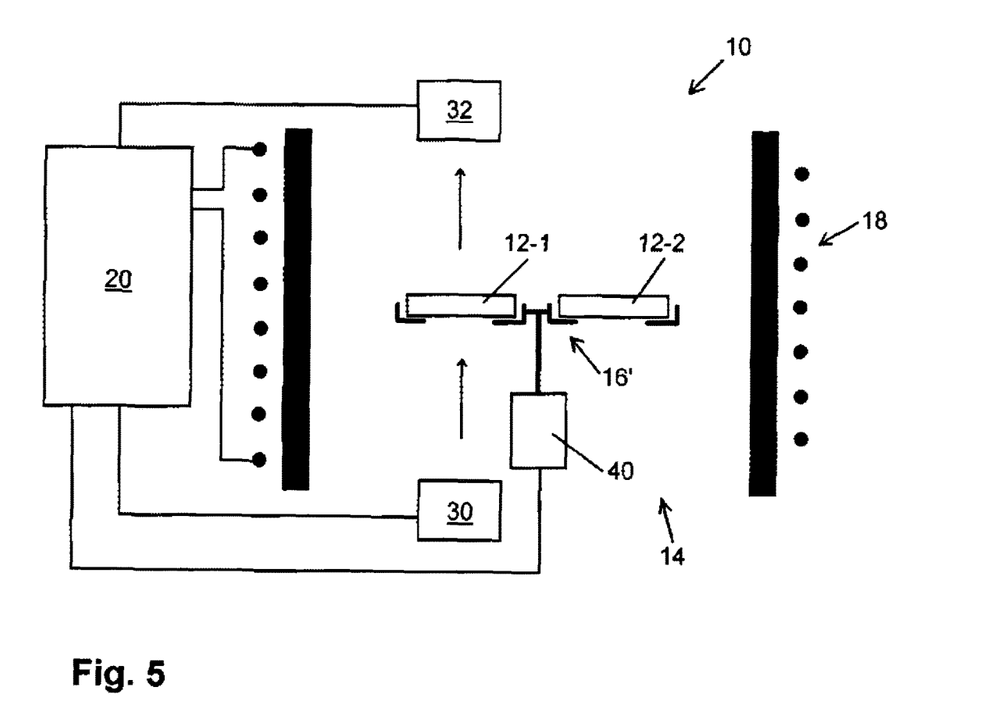
FIG. 5 shows a device for the thermal analysis of a sample according to a further exemplary embodiment.

FIG. 5 shows a device 10 for the thermal analysis of a sample according to a modified exemplary embodiment.

A first (optional) modification as compared to the example according to FIG. 1 is that the device 10 has a controllable multiple sample holder 16' comprising a plurality of accommodations for the corresponding accommodation of a plurality of samples in a temperable sample chamber 14. Two such accommodations for accommodating two samples 12-1 and 12-2 are shown in FIG. 5 in an exemplary manner. In the course of the temperature program, the automatic sample changer 16' can be controlled (here rotated) via an electric drive 40 in such a manner that a desired one of the samples 12-1 and 12-2 can in each case be brought into the beam path of the "temperature conductivity thermometer" formed from the irradiation source 30 and a detection device 32.

A second (optional) modification of the device 10 shown in FIG. 5 is that the arrangement and the operation of a conventional temperature measuring device (see thermal element 22 in FIG. 1) is foregone, and that at least one of the samples 12-1 and 12-2 is instead brought into the beam path of the temperature conductivity thermometer, which is formed from the components 30 and 32, by means of the automatic sample changer 16 for the temperature measuring during normal operation, so as to determine a current temperature T in the sample chamber 14 in the manner as already described above.

In contrast to the illustrated multiple sample holder 16' comprising only two sample accommodations, the sample holder could also be embodied for accommodating at least three (or even more) samples. This has the advantage, e.g., that a plurality of "further samples" with a known such temperature dependency can be used as temperature conductivity thermometers in the course of a thermal analysis on a sample comprising an unknown temperature dependency of the temperature conductivity, whereby an advantageous redundancy of the temperature measuring is created by means of a plurality of such further samples (e.g. in that an average value of the individual results of the temperature measurements is used as determined temperature).

In contrast to the illustrated multiple sample holder 16' comprising only two sample accommodations, the sample holder could also be embodied for accommodating at least three (or even more) samples. This has the advantage, e.g., that a plurality of "further samples" with a known such temperature dependency can be used as temperature conductivity thermometers in the course of a thermal analysis on a sample comprising an unknown temperature dependency of the temperature conductivity, whereby an advantageous redundancy of the temperature measuring is created by means of a plurality of such further samples (e.g. in that an average value of the individual results of the temperature measurements is used as determined temperature).

What is claimed is:

1. A method for thermal analysis of a sample, comprising:
   tempering the sample according to a temperature program, in the course of which a temperature of the sample is changed;
   measuring the temperature of the sample in the course of the temperature program;
   wherein the measuring of the temperature of the sample comprises:
   irradiating a first surface area of the sample with an electromagnetic excitation beam, detecting an intensity of a thermal radiation emanating from a second surface area of the sample as a result of the irradiation;
   determining a temperature conductivity of the sample by evaluating the detected intensity of the thermal radiation; and
   determining the temperature of the sample by means of the determined temperature conductivity by using data, which specify a temperature-dependent course of the temperature conductivity of the sample.

2. A method for thermal analysis of a sample, comprising:
   tempering the sample according to a temperature program, in the course of which a temperature of the sample is changed;
   measuring the temperature of the sample in the course of the temperature program;
   wherein the measuring of the temperature of the sample comprises:
   arranging a further sample adjacent to the sample, so as to subject the sample and the further sample to the tempering together;
   irradiating a first surface area of the further sample with an electromagnetic excitation beam, detecting an intensity of a thermal radiation emanating from a second surface area of the further sample as a result of the irradiation;
   determining a temperature conductivity of the further sample by evaluating the detected intensity of the thermal radiation; and
   determining the temperature of the sample by means of the determined temperature conductivity of the further sample by using data, which specify a temperature-dependent course of the temperature conductivity of the further sample.

3. A method for calibrating a temperature measuring device used in a device for thermal analysis of a sample for measuring a temperature of the sample, comprising:
   arranging a sample in the device for the thermal analysis;
   tempering the sample according to a temperature program, in the course of which a temperature of the sample is changed;
   obtaining a first temperature measurement of the sample in the course of the temperature program by means of the temperature measuring device;
   obtaining a second temperature measurement of the sample in the course of the temperature program by means of the following steps:
   irradiating a first surface area of the sample with an electromagnetic excitation beam, detecting an intensity of a thermal radiation emanating from a second surface area of the sample as a result of the irradiation;
   determining a temperature conductivity of the sample by evaluating the detected intensity of the thermal radiation;
   determining the temperature of the sample by means of the determined temperature conductivity by using data, which specify a temperature-dependent course of the temperature conductivity of the sample, and
   calibrating the temperature measuring device by means of a comparison of results of the first temperature measurement and the second temperature measurement of the sample.

4. A device for thermal analysis of a sample, comprising:
   a sample chamber having a sample holder configured to hold at least one sample;
   a heating device configured for tempering the at least one sample, in the course of which a temperature of the sample is changed;
   a controller controlling the heating device according to a temperature program;
   a temperature sensor disposed within the sample chamber and connected to the controller, the temperature sensor measuring the temperature of the sample in the course of the temperature program;

an irradiator exposing a first surface area of the at least one sample with an electromagnetic excitation beam; and
a detector detecting an intensity of a thermal radiation emanating from a second surface area of the sample as a result of irradiation by the irradiator;
wherein the controller has an evaluator that determines a temperature conductivity of the at least one sample by evaluating the detected intensity of the thermal radiation and determines the temperature of the at least one sample by means of the determined temperature conductivity by using data which specify a temperature-dependent course of the temperature conductivity of the at least one sample.

5. A computer program product comprising:
a program code, which, when executed on a data processing device, carries out a method for thermal analysis of at least one sample, the program code including code to:
temper the at least one sample according to a temperature program, in the course of which a temperature of the sample is changed;
measure the temperature of the sample in the course of the temperature program;
wherein the code to measure the temperature of the at least one sample includes code to:
irradiate a first surface area of the at least one sample with an electromagnetic excitation beam, detecting an intensity of a thermal radiation emanating from a second surface area of the at least one sample as a result of the irradiation;
determine a temperature conductivity of the at least one sample by evaluating the detected intensity of the thermal radiation; and
determine the temperature of the at least one sample by means of the determined temperature conductivity by using data, which specify a temperature-dependent course of the temperature conductivity of the at least one sample.

6. A device for thermal analysis of a sample, comprising:
a sample chamber having a sample holder configured to hold a first sample and a second sample adjacent to the first sample;
a heating device tempering the first sample, in the course of which a temperature of the first sample is changed, wherein the second sample is adjacent to the first sample such that the second sample is tempered along with the first sample;
a controller controlling the heating device according to a temperature program;
a temperature sensor disposed within the sample chamber and connected to the controller, the temperature sensor measuring the temperature of the first sample in the course of the temperature program;
an irradiator exposing a first surface area of the second sample with an electromagnetic excitation beam; and
a detector detecting an intensity of a thermal radiation emanating from a second surface area of the second sample as a result of irradiation by the irradiator;
wherein the controller has an evaluator that determines a temperature conductivity of the second sample by evaluating the detected intensity of the thermal radiation and determines the temperature of the first sample by means of the determined temperature conductivity of the second sample by using data which specify a temperature-dependent course of the temperature conductivity of the second sample.

7. A computer program product comprising:
a program code, which, executed on a data processing device, carries out a method for thermal analysis of a sample, the program code including code to:
temper the sample according to a temperature program, in the course of which a temperature of the sample is changed;
measure the temperature of the sample in the course of the temperature program;
wherein the code to measure the temperature of the sample includes code to:
temper the sample together with a further sample, the further sample being arranged adjacent to the sample;
irradiate a first surface area of the further sample with an electromagnetic excitation beam, and detect an intensity of a thermal radiation emanating from a second surface area of the further sample as a result of the irradiation;
determine a temperature conductivity of the further sample by evaluating the detected intensity of the thermal radiation;
determine the temperature of the sample by means of the determined temperature conductivity of the further sample by using data, which specify a temperature-dependent course of the temperature conductivity of the further sample.

8. A device for calibrating a temperature measuring device that is used in a device for thermal analysis of a sample, the temperature measuring device being configured to measure a temperature of the sample, comprising:
a controller configured to perform the steps of:
tempering at least one sample according to a temperature program, in the course of which a temperature of the at least one sample is changed, the at least one sample being arranged in the device for thermal analysis;
obtaining a first temperature measurement of the at least one sample in the course of the temperature program by means of the temperature measuring device;
obtaining a second temperature measurement of the at least one sample in the course of the temperature program by means of:
irradiating a first surface area of the at least one sample with an electromagnetic excitation beam, detecting an intensity of a thermal radiation emanating from a second surface area of the at least one sample as a result of the irradiation,
determining a temperature conductivity of the at least one sample by evaluating the detected intensity of the thermal radiation, and
determining the temperature of the at least one sample by means of the determined temperature conductivity by using data, which specify a temperature-dependent course of the temperature conductivity of the at least one sample; and
calibrating the temperature measuring device by means of a comparison of results of the first temperature measurement and the second temperature measurement of the sample.

9. A computer program product comprising:
a program code, which, when executed on a data processing device, carries out a method for calibrating a temperature measuring device that is used in a device for thermal analysis of a sample, the temperature measuring device being configured to measure a temperature of at least one sample, the program code including code to:

temper the at least one sample according to a temperature program, in the course of which a temperature of the sample is changed, the at least one sample being arranged in the device for thermal analysis;

obtain a first temperature measurement of the at least one sample in the course of the temperature program by means of the temperature measuring device;

obtain a second temperature measurement of the at least one sample in the course of the temperature program by means of:

irradiating a first surface area of the at least one sample with an electromagnetic excitation beam, detecting an intensity of a thermal radiation emanating from a second surface area of the at least one sample as a result of the irradiation, determining a temperature conductivity of the at least one sample by evaluating the detected intensity of the thermal radiation, and determining the temperature of the at least one sample by means of the determined temperature conductivity by using data, which specify a temperature-dependent course of the temperature conductivity of the at least one sample; and calibrate the temperature measuring device by means of a comparison of results of the first temperature measurement and the second temperature measurement of the at least one sample.

10. A method for thermal analysis of a sample comprising:

tempering at least one sample according to a temperature program, in the course of which a temperature of the at least one sample is changed, taking at least two measurements of the at least one sample in the course of the temperature program, wherein a first of the at least two measurements measures a temperature of a first sample of the at least one sample;

wherein a second of the at least two measurements measures at least one physical characteristic of the first sample, in the course of the temperature program, wherein the measuring of the temperature of the first sample comprises:

irradiating a first surface area of the first sample with an electromagnetic excitation beam, detecting an intensity of a thermal radiation emanating from a second surface area of the first sample as a result of the irradiation, determining a temperature conductivity of the first sample by evaluating the detected intensity of the thermal radiation, determining the temperature of the first sample by means of the determined temperature conductivity by using data, which specify a temperature-dependent course of the temperature conductivity of the first sample, and storing the first and second of the at least two measurements as time-resolved data.

11. The method of claim 10, wherein the second of the at least two measurements measures at least one physical characteristic of the first sample, which differs from the temperature of the first sample, in the course of the temperature program.

12. The method of claim 10, further comprising arranging a further sample adjacent to the first sample, so as to subject the first sample and the further sample to the tempering together;

irradiating a first surface area of the further sample with an electromagnetic excitation beam, detecting an intensity of a thermal radiation emanating from a second surface area of the further sample as a result of the irradiation;

determining a temperature conductivity of the further sample by evaluating the detected intensity of the thermal radiation; and determining the temperature of the first sample by means of the determined temperature conductivity of the further sample by using data, which specify a temperature-dependent course of the temperature conductivity of the further sample.

13. The method of claim 10, wherein the temperature of the first sample in the course of the temperature program is measured by a temperature measuring device.

14. The method of claim 13, further including calibrating the temperature measuring device by comparing results of the first and second measurements.

* * * * *